(12) United States Patent
Lee et al.

(10) Patent No.: US 8,742,005 B2
(45) Date of Patent: Jun. 3, 2014

(54) ACRYLATE-BASED COMPOUNDS AND PHOTOSENSITIVE COMPOSITION COMPRISING THE SAME

(75) Inventors: Keon Woo Lee, Daejeon (KR); Sang Kyu Kwak, Daejeon (KR); Changsoon Lee, Daejeon (KR); Hyehyeon Kim, Seoul (KR)

(73) Assignee: LG Chem, Ltd., Seoul (KR)

( * ) Notice: Subject to any disclaimer, the term of this patent is extended or adjusted under 35 U.S.C. 154(b) by 112 days.

(21) Appl. No.: 13/300,055

(22) Filed: Nov. 18, 2011

(65) Prior Publication Data

US 2012/0156619 A1  Jun. 21, 2012

(30) Foreign Application Priority Data

Nov. 19, 2010 (KR) .......................... 10-2010-0115556

(51) Int. Cl.
*G03F 7/32* (2006.01)
*C07C 69/94* (2006.01)
*C07C 69/602* (2006.01)
*G03F 7/027* (2006.01)
*G03F 7/033* (2006.01)
*G03F 7/032* (2006.01)
*C07C 69/92* (2006.01)

(52) U.S. Cl.
CPC .............. *G03F 7/027* (2013.01); *G03F 7/033* (2013.01); *G03F 7/032* (2013.01); *C07C 69/92* (2013.01); *C07C 69/94* (2013.01); *C07C 69/602* (2013.01)

USPC ........... 524/559; 524/556; 560/193; 560/194; 560/67; 560/100; 560/130; 562/400; 562/405; 562/490; 562/491; 562/492

(58) Field of Classification Search
USPC ................ 560/8, 64, 67, 100, 130, 193, 194; 562/400, 405, 490, 491, 492
See application file for complete search history.

(56) References Cited

U.S. PATENT DOCUMENTS 4,604,342 A * 8/1986 Sondergeld et al. ........ 430/281.1
5,320,886 A * 6/1994 Bowen ......................... 428/34.1

FOREIGN PATENT DOCUMENTS

JP  2006243493 A * 9/2006
JP  2010072389 A * 4/2010

OTHER PUBLICATIONS

English Translation of Fujimaki; JP 2006-243493 A; Sep. 2006.*

* cited by examiner

*Primary Examiner* — Mark Kaucher
(74) *Attorney, Agent, or Firm* — Rothwell, Figg, Ernst & Manbeck, P.C.

(57) ABSTRACT

The present invention relates to an acrylate-based compound that includes an organic acid having two or more acrylate groups and one or more phenolic acid structures in one molecule, and a photosensitive composition including the same. It is possible to shorten a developing time in a photolithography process without damaging photosensitivity by using the photosensitive composition according to the present invention.

18 Claims, 2 Drawing Sheets

ACRYLATE-BASED COMPOUNDS AND PHOTOSENSITIVE COMPOSITION COMPRISING THE SAME

CROSS-REFERENCE TO RELATED APPLICATIONS

This application claims priority to and the benefit of Korean Patent Application No. 10-2010-0115556 filed in the Korean Intellectual Property Office on Nov. 19, 2010, the entire contents of which are incorporated herein by reference.

TECHNICAL FIELD

The present invention relates to acrylate-based compounds that can increase a developing property of a photosensitive composition, and a photosensitive composition comprising the same.

BACKGROUND

In manufacturing a color filter of a liquid crystal display diode, a photosensitive composition is used as an essential material. For example, a color pixel exhibiting a color, a black matrix for blocking light, an overcoat to compensate for a step between pixels, and a column spacer maintaining a cell-gap of a liquid crystal display diode are all formed of a thin film layer that is formed by using a photosensitive composition by a photolithography process and has a thickness of 5 μm or less.

Recently, the liquid crystal display diode is widely used from a mobile phone, in which a width of the diode is about 1 inch, to a TV in which a width of the diode is above 50 inches. In accordance with enlargement of the display diode and an improvement in productivity, recently, a manufacturing manner using a glass substrate having a large area is preferred.

In the case where the display diode is manufactured by using the glass substrate having the large area, a possibility that the glass substrate is not completely washed but residuals remain after a developing process is increased. Accordingly, in general, a problem that the residuals remain is solved by increasing a flow rate, a temperature or a process time of the developing solution of equipment. This causes a decrease in productivity, which is pointed out as a disadvantage removing a merit of improving productivity by using the glass substrate having the large area.

In the case of the most photosensitive compositions, in order to make up for the disadvantage, a method for increasing an acid value or for decreasing hardness of a thin film after drying has been used. However, according to this method, since a developing property is improved, but sensitivity of the pattern is decreased and thickness stability of the pattern is deteriorated, this method is not considered as a basic solution. Accordingly, there is a need to develop a novel material increasing a developing property and maintaining photosensitivity.

SUMMARY OF THE INVENTION

The present invention has been made in an effort to provide an acrylate-based compound that can improve a developing property without damaging photosensitivity, and a photosensitive composition including the same.

An exemplary embodiment of the present invention provides an acrylate-based compound represented by the following Formula 1:

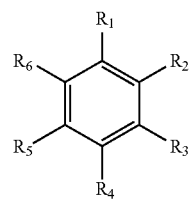

[Formula 1]

wherein at least one of $R_1$ to $R_6$ is —OH or —COOH, at least two of $R_1$ to $R_6$ are each independently represented by the following Formula 2 or Formula 3, and the rest are selected from the group consisting of hydrogen, a halogen group, an alkyl group having 1 to 5 carbon atoms, an alkoxy group having 1 to 5 carbon atoms, and a haloalkyl group having 1 to 5 carbon atoms.

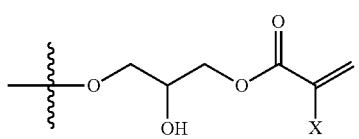

[Formula 2]

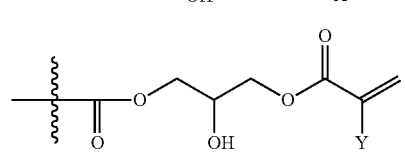

[Formula 3]

wherein

X and Y are each independently selected from the group consisting of hydrogen, a halogen group, an alkyl group having 1 to 5 carbon atoms, an alkoxy group having 1 to 5 carbon atoms, and a haloalkyl group having 1 to 5 carbon atoms.

Another exemplary embodiment of the present invention provides an acrylate-based compound represented by the following Formula 4:

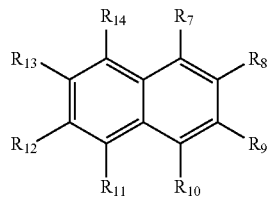

[Formula 4]

wherein at least one of $R_7$ to $R_{14}$ is —OH or —COOH, at least two of $R_7$ to $R_{14}$ are each independently represented by Formula 2 or Formula 3, and the rest are selected from the group consisting of hydrogen, a halogen group, an alkyl group having 1 to 5 carbon atoms, an alkoxy group having 1 to 5 carbon atoms, and a haloalkyl group having 1 to 5 carbon atoms.

Another exemplary embodiment of the present invention provides an acrylate-based compound represented by the following Formula 5:

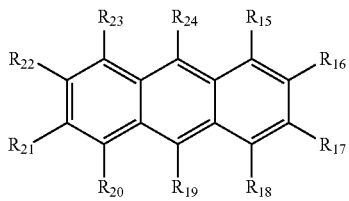

[Formula 5]

wherein at least one of $R_{15}$ to $R_{24}$ is —OH or —COOH, at least two of $R_{15}$ to $R_{24}$ are each independently represented by Formula 2 or Formula 3, and the rest are selected from the group consisting of hydrogen, a halogen group, an alkyl group having 1 to 5 carbon atoms, an alkoxy group having 1 to 5 carbon atoms, and a haloalkyl group having 1 to 5 carbon atoms.

Another exemplary embodiment of the present invention provides a composition for improving a developing property, including: one or more compounds of acrylate-based compounds represented by Formula 1, Formula 4, and Formula 5.

Another exemplary embodiment of the present invention provides a photosensitive composition, including: a binder resin including an alkali soluble polymer resin; a crosslinking compound; a photopolymerization initiator; one or more compounds of acrylate-based compounds represented by Formula 1, Formula 4, and Formula 5; and a solvent.

Another exemplary embodiment of the present invention provides a sensitive material including the photosensitive composition.

According to the exemplary embodiments of the present invention, since the acrylate-based compound includes at least one organic acid group and at least two acrylate groups simultaneously with the benzene, naphthalene, or anthracene structure as the center, the compound may be more usefully applied to the photosensitive composition. The photosensitive composition according to the exemplary embodiment of the present invention may shorten the developing time in a photolithography process without damaging photosensitivity.

DETAILED DESCRIPTION

Figure 1:
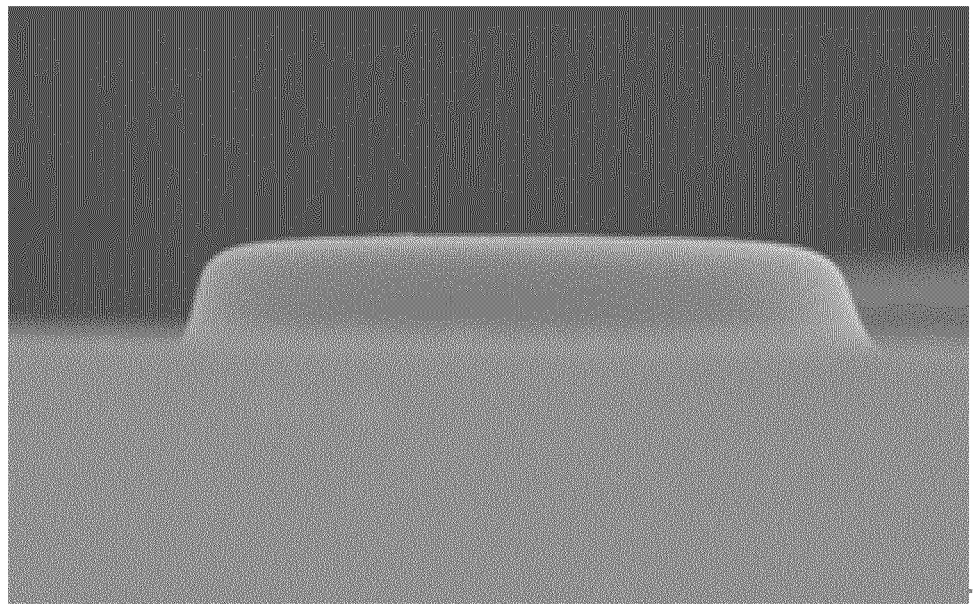
FIG. 1 illustrates results of observing whether a pattern is formed or not by a scanning electron microscope after developing is performed by using a composition of Example 1.

Hereinafter, the present invention will be described in detail.

An acrylate-based compound according to an exemplary embodiment of the present invention is represented by Formula 1, Formula 4 or Formula 5.

The compound represented by Formula 1, Formula 4 or Formula 5 includes at least one organic acid group and at least two acrylate groups simultaneously with the benzene, naphthalene, or anthracene structure as the center.

In the acrylate-based compound according to the exemplary embodiment of the present invention, substituent groups of Formula 1, Formula 4 and Formula 5 will be described in more detail below.

As the halogen group, there may be —F, —Cl, —Br, and —I, but the group is not limited thereto.

The alkyl group may be a straight or branched chain, and the number of carbon atoms is not particularly limited but may be 1 to 5. As detailed examples thereof, there are a methyl group, an ethyl group, a propyl group, an isopropyl group, a butyl group, and a t-butyl group, but the examples are not limited thereto.

The alkoxy group may have 1 to 5 carbon atoms, more specifically, there may be methoxy, ethoxy, and isopropyloxy, but the group is not limited thereto.

The haloalkyl group may have 1 to 5 carbon atoms, and means a functional group in which one or more hydrogens of the alkyl group are substituted by the halogen group.

Detailed examples of the functional group represented by Formula 2 are provided below, but are not limited thereto.

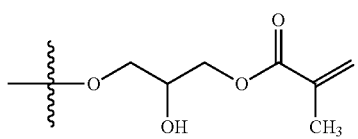

[Formula 6]

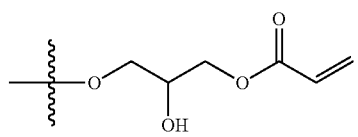

[Formula 7]

Specific examples of the functional group represented by Formula 3 are provided below, but are not limited thereto.

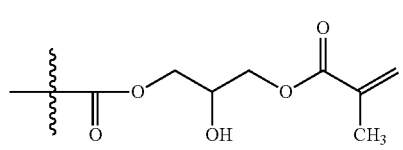

[Formula 8]

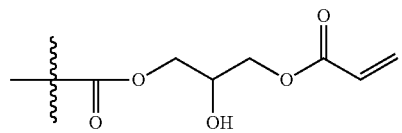

[Formula 9]

The composition for improving a developing property according to the exemplary, embodiment of the present invention includes the acrylate-based compound.

The composition for improving a developing property may be a photosensitive composition which will be described below.

The composition for improving a developing property according to the exemplary embodiment of the present invention may include one or more compounds of acrylate-based compounds represented by Formula 1, Formula 4, and Formula 5.

The acrylate-based compound according to the exemplary embodiment of the present invention includes a structure of a phenolic acid or a benzoic acid in addition to acrylate or methacrylate that can perform a crosslinking reaction in a molecule. Since the phenolic acid or benzoic acid participates in a neutralization reaction with a developing solution in which an alkali aqueous solution such as KOH, $Na_2CO_3$, $NaHCO_3$, and tetramethyl ammonium hydroxide is used as a base, the acid helps improve the developing property.

According to the exemplary embodiments of the present invention, since the acrylate-based compound includes at least one organic acid and at least two acrylate groups simultaneously with the benzene, naphthalene, or anthracene structure as the center, the compound may be more usefully applied to the photosensitive composition. The photosensitive composition according to the exemplary embodiment of the present invention may shorten the developing time in a photolithography process without damaging photosensitivity.

For example, the acrylate-based compound represented by Formula 1 may be manufactured by the following reaction. If 3,5-dihydroxy benzoic acid and glycidyl methacrylate are reacted while an equivalent is controlled, the organic acid of the 3,5-dihydroxy benzoic acid and the glycidyl group of glycidyl methacrylate are reacted, and thus, the following mixture is, obtained. Therefore, various compounds represented by Formula 1 may be synthesized through the reaction of a material having a structure including several benzoic acids or phenolic acids and glycidyl acrylate or glycidyl methacrylate.

Preparation Example 1

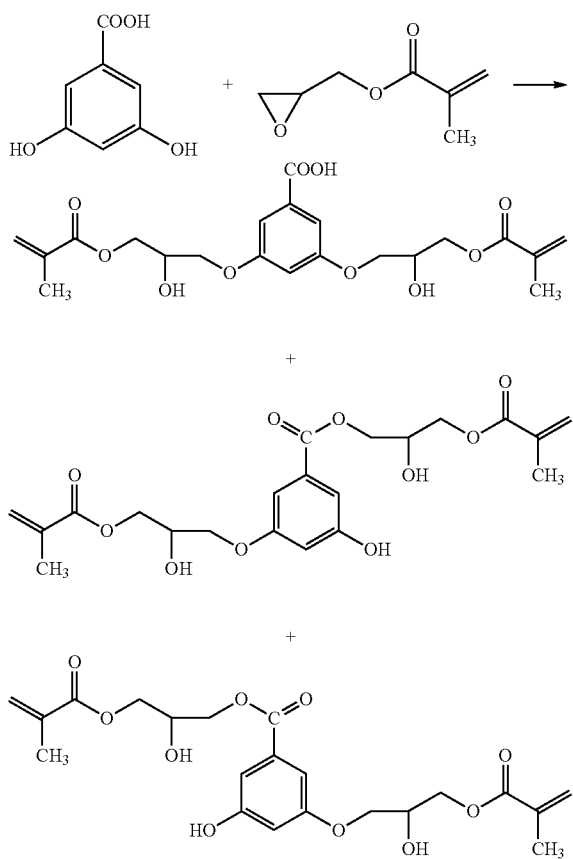

The acrylate-based compound represented by Formula 4 or Formula 5 may be synthesized by a similar manufacturing method.

The photosensitive composition according to the exemplary embodiment of the present invention includes a binder resin including an alkali soluble polymer resin; a crosslinking compound; a photopolymerization initiator; one or more compounds of acrylate-based compounds represented by Formula 1, Formula 4, and Formula 5; and a solvent.

In the photosensitive composition according to the exemplary embodiment of the present invention, the total content of the acrylate-based compound represented by Formula 1, Formula 4, or Formula 5 is preferably 0.8 to 4 wt % on the basis of the total weight of the photosensitive composition. In the case where the content of the acrylate-based compound is 0.8 wt % or more on the basis of the total weight of the photosensitive composition, a developing property improving effect is increased, and in the case where the content is 4 wt % or less, it is possible to prevent deterioration in photosensitivity.

In the photosensitive composition according to the exemplary embodiment of the present invention, the total content of the acrylate-based compound represented by Formula 1, Formula 4, or Formula 5 is preferably 5 to 25 wt % on the basis of the weight of the crosslinking compound. In the case where the content of the acrylate-based compound is 5 wt % or more on the basis of the weight of the crosslinking compound, a developing property improving effect is increased, and in the case where the content is 25 wt % or less, it is possible to prevent deterioration in photosensitivity.

Since the photosensitive composition according to the exemplary embodiment of the present invention includes the binder resin, there is an effect of controlling viscosity and there is an effect of making patterning using an alkali developing solution possible.

In the photosensitive composition according to the exemplary embodiment of the present invention, as the binder resin, matters that are generally used in the art such as the alkali soluble binder resin may be used. Specifically, an acryl-based binder resin including a carboxyl group may be used, and more specifically, a matter that is configured by copolymerizing a monomer providing mechanical strength of the film and a monomer providing alkali solubility may be used.

As the monomer that can be used for controlling mechanical strength of the film, for example, one or more selected from unsaturated ester carboxylates such as benzyl(metha)acrylate, methyl(metha)acrylate, ethyl(metha)acrylate, butyl(metha)acrylate, dimethylaminoethyl(metha)acrylate, isobutyl(metha)acrylate, t-butyl(metha)acrylate, cyclohexyl(metha)acrylate, isobornyl(metha)acrylate, ethylhexyl(metha)acrylate, 2-phenoxyethyl(metha)acrylate, tetrahydrofurfuryl(metha)acrylate, hydroxyethyl(metha)acrylate, 2-hydroxypropyl(metha)acrylate, 2-hydroxy-3-chloropropyl(metha)acrylate, 4-hydroxybutyl(metha)acrylate, glycerol(metha)acrylate, 2-methoxyethyl(metha)acrylate, 3-methoxybutyl(metha)acrylate, ethoxydiethyleneglycol(metha)acrylate, methoxytriethyleneglycol(metha)acrylate, methoxytripropyleneglycol(metha)acrylate, poly(ethylene glycol)methylether(metha)acrylate, phenoxydiethyleneglycol(metha)acrylate, p-nonylphenoxypolyethyleneglycol(metha)acrylate, p-nonylphenoxypolypropyleneglycol(metha)acrylate, glycidyl(metha)acrylate, dicyclopentanyl(metha)acrylate, dicyclopentenyl(metha)acrylate, dicyclopentenyloxyethyl(metha)acrylate, isobonyl(metha)acrylate, adamentyl(metha)acrylate, stearyl(metha)acrylate, hexyl(metha)acrylate, heptyl(metha)acrylate, oxyl(metha)acrylate, nonyl(metha)acrylate, decyl(metha)acrylate, laurylmethacrylate, methyl α-hydroxymethyl acrylate, ethyl α-hydroxymethyl acrylate, propyl α-hydroxymethyl acrylate, and butyl α-hydroxymethyl acrylate may be used, but the monomer is not limited thereto.

As the monomer providing alkali solubility, for example, one or more selected from the group consisting of (metha)acrylic acid, crotonic acid, itaconic acid, maleic acid, fumaric acid, monomethyl maleic acid, 5-nobonen 2-carboxylic acid, mono-2-((metha)acryloyloxy)ethyl phthalate, mono-2-((metha)acryloyloxy)ethyl succinate, and ω-carboxypolycaprolactone mono(metha)acrylate are preferably used, but the monomer is not limited thereto. For the binder resin, specifically, a weight average molecular weight may be 3,000 to 150,000. If the molecular weight is 3,000 or more, there is an effect of preventing the pattern from being lost during the developing process, and if the molecular weight is less than 150,000, there is an effect of preventing a problem that it is difficult to perform coating because viscosity is increased.

The content of the binder resin may be 1 to 20 wt % on the basis of the total weight of the photosensitive composition, but is not limited thereto. If the content of the binder resin is 1 wt % or more, there is an effect in which pattern can be performed by using the alkali aqueous solution, if the content is less than 20 wt %, there is an effect of preventing the pattern from being lost during the developing process.

In the photosensitive composition according to the exemplary embodiment of the present invention, as the crosslinking compound, specifically, a crosslinking compound including an ethylene-based unsaturated group may be used, and more specifically, a crosslinking compound including two or more unsaturated acryl groups, and a crosslinking compound including three or more unsaturated acryl groups may be used. Specific examples thereof may include one or more selected from the group consisting of a compound that is obtained by esterifying polyvalent alcohol such as ethyleneglycol di(metha)acrylate, polyethylene glycol di(metha)acrylate in which the number of ethylene groups is 2 to 14, trimethylolpropane di(metha)acrylate, trimethylolpropane tri(metha)acrylate, pentaerythritol tri(metha)acrylate, pentaerythritol tetra(metha)acrylate, 2-trisacryloyloxymethylethyl phthalate, propylene glycol di(metha)acrylate in which the number of propylene groups is 2 to 14, dipentaerythritol penta(metha)acrylate, dipentaerythritol hexa(metha)acrylate, and a mixture of an acidic denatured material of dipentaerythritol penta(metha)acrylate and dipentaerythritol hexa(metha)acrylate (trademark: TO-2348, and TO-2349 manufactured by Toagosei Co., Ltd. in Japan) by a α,β-unsaturated carboxylic acid; a compound that is obtained by adding a (metha)acrylic acid to a compound including a glycidyl group such as an addition product of trimethylolpropane triglycidyletheracrylic acid and an addition product of bisphenol A diglycidyletheracrylic acid; a hydroxyl group such as diester phthalate of β-hydroxyethyl(metha)acrylate and an addition product of toluene diisocyanate of β-hydroxyethyl(metha)acrylate, or an addition product of a compound having an ethylene unsaturated bond and an ester compound with polyvalent carboxylic acid or polyisocyanate; (metha)acrylate alkylester such as methyl(metha)acrylate, ethyl(metha)acrylate, butyl(metha)acrylate, and 2-ethylhexyl(metha)acrylate; and 9,9'-bis[4-(2-acryloyloxyethoxy)phenyl]fluorine, but are not limited thereto, and a general matter that is known in the art may be used. In some cases, a silica dispersion element may be used in these compounds, for example, there are Nanocryl XP series (0596, 1045, 21/1364) and Nanopox XP series (0516, 0525) manufactured by Hanse Chemie Co., Ltd.

The content of the crosslinking compound may be 1 to 30 wt % on the basis of the total weight of the photosensitive composition, but is not limited thereto.

In the photosensitive composition according to the exemplary embodiment of the present invention, as the photopolymerization initiator, for example, a triazine-based compound such as 2,4-trichloromethyl-(4'-methoxyphenyl)-6-triazine, 2,4-trichloromethyl-(4'-methoxystyryl)-6-triazine, 2,4-trichloromethyl-(fipronil)-6-triazine, 2,4-trichloromethyl-(3',4'-dimethoxyphenyl)-6-triazine, 3-(4-[2,4-bis(trichloromethyl)-s-triazine-6-yl]phenylthio)propanoic acid, 2,4-trichloromethyl-(4'-ethylbiphenyl)-6-triazine, and 2,4-trichloromethyl-(4'-methylbiphenyl)-6-triazine; a biimidazole compound such as 2,2'-bis(2-chlorophenyl)-4,4',5,5'-tetraphenyl biimidazole, and 2,2'-bis(2,3-dichlorophenyl)-4,4',5,5'-tetraphenyl biimidazole; an acetophenone-based compound such as 2-hydroxy-2-methyl-1-phenylpropane-1-one, 1-(4-isopropylphenyl)-2-hydroxy-2-methylpropane-1-one, 4-(2-hydroxyethoxy)-phenyl(2-hydroxy)propyl ketone, 1-hydroxycyclohexyl phenyl ketone, 2,2-dimethoxy-2-phenyl acetophenone, 2-methyl-(4-methylthiophenyl)-2-morpholino-1-propane-1-one (Irgacure-907), and 2-benzyl-2-dimethylamino-1-(4-morpholinophenyl)-butane-1-one (Irgacure-369); an O-acyloxime-based compound such as Irgacure OXE 01 and Irgacure OXE 02 manufactured by Ciba Geigy Co., Ltd.; a benzophenone-based compound such as 4,4'-bis(dimethylamino)benzophenone, and 4,4'-bis(diethylamino)benzophenone; a thioxantone-based compound such as 2,4-diethyl thioxantone, 2-chloro thioxantone, isopropyl thioxantone, diisopropyl thioxantone; a phosphine oxide-based compound such as 2,4,6-trimethylbenzoyl diphenylphosphine oxide, bis(2,6-dimethoxybenzoyl)-2,4,4-trimethylpentyl phosphine oxide, and bis(2,6-dichlorobenzoyl) propyl phosphine oxide; and a coumarine-based compound such as 3,3'-carbonylvinyl-7-(diethylamino)coumarine, 3-(2-benzothiazolyl)-7-(diethylamino)coumarine, 3-benzoyl-7-(diethylamino)coumarine, 3-benzoyl-7-methoxy-coumarine, and 10,10'-carbonylbis[1,1,7,7-tetramethyl-2,3,6,7-tetrahydro-1H,5H,11H—C1]-benzopyrano[6,7,8-ij]-quinolizine-11-one may be used alone or in a mixture of two or more.

The content of the photopolymerization initiator may be 0.1 to 5 wt % on the basis of the total weight of the photosensitive composition, but is not limited thereto.

The solvent, for example, may include one or more selected from the group consisting of methyl ethyl ketone, methyl cellosolve, ethyl cellosolve, ethyleneglycol dimethyl ether, ethyleneglycol diethyl ether, propyleneglycol dimethyl ether, propyleneglycol diethyl ether, diethyleneglycol dimethylether, diethyleneglycol diethylether, diethyleneglycol methyl ethyl ether, 2-ethoxy propanol, 2-methoxy propanol, 3-methoxy butanol, cyclohexanone, cyclopentanone, propyleneglycol methyl ether acetate, propyleneglycol ethyl ether acetate, 3-methoxybutyl acetate, ethyl 3-ethoxypropionate, ethyl cellosolveacetate, methyl cellosolveacetate, butyl acetate, and dipropyleneglycol monomethyl ether, but is not necessarily limited thereto.

The content of the solvent may be 45 to 95 wt % on the basis of the total weight of the photosensitive composition, but is not limited thereto.

The photosensitive composition according to the exemplary embodiment of the present invention may further include one or more selected from the group consisting of a colorant, a curing accelerator, a thermal polymerization inhibitor, a surfactant, a photosensitizer, a plasticizer, an adhesion promoter, a filler, and an adhesive preparation according to the purpose.

As the colorant, one more pigments, dyes, or mixtures thereof may be used. Specifically, as a black pigment, metal oxide such as carbon black, graphite, and titanium black may be used. As examples of the carbon black, there are Cisto 5HIISAF-HS, Cisto KH, Cisto 3HHAF-HS, Cisto NH, Cisto 3M, Cisto 300HAF-LS, Cisto 116HMMAF-HS, Cisto 116MAF, Cisto FMFEF-HS, Cisto SOFEF, Cisto VGPF, Cisto SVHSRF-HS, and Cisto SSRF manufactured by Donghae Carbon, Co., Ltd.; Diagram black II, Diagram black N339, Diagram black SH, Diagram black H, Diagram LH, Diagram HA, Diagram SF, Diagram N550M, Diagram M, Diagram E, Diagram G, Diagram R, Diagram N760M, Diagram LR, #2700, #2600, #2400, #2350, #2300, #2200, #1000, #980, #900, MCF88, #52, #50, #47, #45, #45L, #25, #CF9, #95, #3030, #3050, MA7, MA77, MA8, MA11, MA100, MA40, OIL7B, OIL9B, OIL11B, OIL30B, and OIL31B manufactured by Mitsubishi Chemical Co., Ltd.; PRINTEX-U, PRINTEX-V, PRINTEX-140U, PRINTEX-140V, PRINTEX-95, PRINTEX-85, PRINTEX-75, PRINTEX-55, PRINTEX-45, PRINTEX-300, PRINTEX-35, PRINTEX-25, PRINTEX-200, PRINTEX-40, PRINTEX-30, PRINTEX-3, PRINTEX-A, SPECIAL BLACK-550, SPECIAL BLACK-350, SPECIAL BLACK-250, SPECIAL BLACK-100, and LAMP BLACK-101 manufactured by Daegussa, Co., Ltd.; and RAVEN-1100ULTRA, RAVEN-1080ULTRA, RAVEN-1060ULTRA, RAVEN-1040, RAVEN-1035, RAVEN-1020, RAVEN-1000, RAVEN-890H, RAVEN-890, RAVEN-880ULTRA, RAVEN-860ULTRA, RAVEN-850, RAVEN-820, RAVEN-790ULTRA, RAVEN-780ULTRA, RAVEN-760ULTRA, RAVEN-520, RAVEN-500, RAVEN-460, RAVEN-450, RAVEN-430ULTRA, RAVEN-420, RAVEN-410, RAVEN-2500ULTRA, RAVEN-2000, RAVEN-1500, RAVEN-1255, RAVEN-1250, RAVEN-1200, RAVEN-1190ULTRA, and RAVEN-1170 manufactured by Columbia Carbon Co., Ltd., or a mixture thereof. As examples of the colorant exhibiting a color, there are carmine 6B (C.I. 12490), phthalocyanine green (C.I. 74260), phthalocyanine blue (C.I. 74160), perylene black (BASF K0084. K0086), cyanine black, linol yellow (C.I. 21090), linol yellow GRO (C.I. 21090), benzidine yellow 4T-564D, victoria pure blue (C.I. 42595), C.I. PIGMENT RED 3, 23, 97, 108, 122, 139, 140, 141, 142, 143, 144, 149, 166, 168, 175, 177, 180, 185, 189, 190, 192, 202, 214, 215, 220, 221, 224, 230, 235, 242, 254, 255, 260, 262, 264, and 272; C.I. PIGMENT GREEN 7 and 36; C.I. PIGMENT blue 15:1, 15:3, 15:4, 15:6, 16, 22, 28, 36, 60, and 64; C.I. PIGMENT yellow 13, 14, 35, 53, 83, 93, 95, 110, 120, 138, 139, 150, 151, 154, 175, 180, 181, 185, 194, and 213; and C.I. PIGMENT VIOLET 15, 19, 23, 29, 32, and 37, and in addition to this, a white pigment and a fluorescent pigment may be used. As the phthalocyanine-based complex compound used as the pigment, a material in which zinc other than copper is used as the central metal may be used. The curing accelerator, for example, may include one or more selected from the group consisting of 2-mercaptobenzoimidazole, 2-mercaptobenzothiazole, 2-mercaptobenzoxazole, 2,5-dimercapto-1,3,4-thiadiazole, 2-mercapto-4,6-dimethylaminopyrydine, pentaerythritol tetrakis(3-mercaptopropionate), pentaerythritol tris(3-mercaptopropionate), pentaerythritol tetrakis(2-mercaptoacetate), pentaerythritol tris(2-mercaptoacetate), trimethylolpropane tris(2-mercaptoacetate), trimethylolpropane tris(3-mercaptopropionate), trimethylolethane tris(2-mercaptoacetate), and trimethylolethane tris(3-mercaptopropionate), but is not limited thereto, and may include matters that are generally known in the art.

The thermal polymerization inhibitor, for example, may include one or more selected from the group consisting of p-anisole, hydroquinone, pyrocatechol, t-butyl catechol, N-nitrosophenylhydroxyamine ammonium salt, N-nitrosophenylhydroxyamine aluminum salt, and phenothiazine, but is not limited thereto, and may include matters that are generally known in the art.

As the surfactant, photosensitizer, plasticizer, adhesion promoter, and filler, all compounds that can be included in a known photosensitive resin composition may be used.

The content of the colorant is preferably 1 to 20 wt % on the basis of the total weight of the photosensitive composition, and the contents of the other additives are each independently preferably 0.01 to 5 weight on the basis of the total weight of the photosensitive composition, but are not limited thereto.

Meanwhile, the transparent photosensitive composition according to the exemplary embodiment of the present invention is used in a roll coater, a curtain coater, a spin coater, a slot die coater, and various printings and precipitations, and may be applied onto a support of metal, paper, glass, and plastic substrates. The composition may be transferred on the other support after being coated on the support such as a film, or may be transferred on a blanket after being coated on a first support and transferred on a second support again, but the application method thereof is not particularly limited.

As a light source for curing the transparent photosensitive composition of the present invention, for example, there are a mercury vapor arc, a carbon arc, and a Xe arc emitting light having a wavelength of 250 to 450 nm, but the light source is not limited thereto.

The photosensitive composition according to the exemplary embodiment of the present invention may be used as a sensitive material selected from the group consisting of a sensitive material for photoacryl, a sensitive material for a touch panel protection material, a pigment dispersion type sensitive material for manufacturing a TFT LCD color filter, a sensitive material for forming a black matrix of a TFT LCD or organic light emitting diode (OLED), a sensitive material for forming an overcoat layer of a LCD or OLED, a column spacer sensitive material, a sensitive material for a printed board or printed circuit board, and a transparent sensitive material. The composition may be used for a material for manufacturing a photocurable paint, a photocurable ink, a photocurable adhesive agent, a printed board, and a PDP, a partition material for an OLED, and a partition material for a LED, but the purpose thereof is not particularly limited.

Hereinafter, preferable Synthetic Examples, Examples, Comparative Examples, and Test Examples will be described in order to help understand the present invention. However, the following Synthetic Examples, Examples, Comparative Examples, and Test Examples are set forth to illustrate the present invention, but the scope of the present invention is not limited thereto.

EXAMPLE

Synthetic Example 1

50 mol of the gallic acid (3,4,5-trihydroxybenzoic acid) was dissolved in acetone using an excessive amount, and agitated, and 150 mol of glycidyl methacrylate was slowly mixed for 1 hour. Next, the mixture that was formed of the compound represented by the following Formula 10 was obtained by purifying the reactant.

[Formula 10]

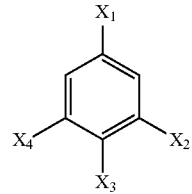

In Formula 10, $X_1$, $X_2$, $X_3$, and $X_4$ are selected from combinations of the following Table 1. The synthesis results are shown through $^1$H NMR.

TABLE 1

| Combination | $X_1$ | $X_2$ | $X_3$ | $X_4$ | $^1$H NMR |
|---|---|---|---|---|---|
| 1 | —C(O)OH | Formula 6 | Formula 6 | Formula 6 | 11.0 ppm (—COOH), 2.0 ppm (—OH aliphatic), 1.9, 6.2, 5.6 ppm (—C(CH$_3$)=CH$_2$), 7.1 ppm (aromatic H) |
| 2 | Formula 8 | —OH | Formula 6 | Formula 6 | 5.0 ppm (—OH phenolic), 2.0 ppm (—OH aliphatic), 1.9, 6.2, 5.6 ppm (—C(CH$_3$)=CH$_2$), 6.9 ppm (aromatic H) |
| 3 | Formula 8 | Formula 6 | —OH | Formula 6 | 5.0 ppm (—OH phenolic), 2.0 ppm (—OH aliphatic), 1.9, 6.2, 5.6 ppm (—C(CH$_3$)=CH$_2$), 6.9 ppm (aromatic H) |
| 4 | Formula 8 | Formula 6 | Formula 6 | —OH | 5.0 ppm (—OH phenolic), 2.0 ppm (—OH aliphatic), 1.9, 6.2, 5.6 ppm (—C(CH$_3$)=CH$_2$), 6.9 ppm (aromatic H) |

Synthetic Example 2

50 mol of the 2,3,4-trihydroxybenzoic acid was dissolved in acetone using an excessive amount, and agitated, and 150 mol of glycidyl methacrylate was slowly mixed for 1 hour. Next, the mixture that was formed of the compound represented by the following Formula 11 was obtained by purifying the reactant.

[Formula 11]

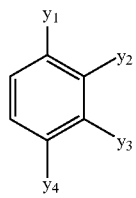

In Formula 11, $y_1$, $y_2$, $y_3$, and $y_4$ are selected from combinations of the following Table 2.

TABLE 2

| Combination | $y_1$ | $y_2$ | $y_3$ | $y_4$ | $^1$H NMR |
|---|---|---|---|---|---|
| 1 | —C(O)OH | Formula 6 | Formula 6 | Formula 6 | 11.0 ppm (—COOH), 2.0 ppm (—OH aliphatic), 1.9, 6.2, 5.6 ppm (—C(CH$_3$)=CH$_2$), 7.1 ppm (aromatic H) |
| 2 | Formula 8 | —OH | Formula 6 | Formula 6 | 5.0 ppm (—OH phenolic), 2.0 ppm (—OH aliphatic), 1.9, 6.2, 5.6 ppm (—C(CH$_3$)=CH$_2$), 6.9 ppm (aromatic H) |
| 3 | Formula 8 | Formula 6 | —OH | Formula 6 | 5.0 ppm (—OH phenolic), 2.0 ppm (—OH aliphatic), 1.9, 6.2, 5.6 ppm (—C(CH$_3$)=CH$_2$), 6.9 ppm (aromatic H) |
| 4 | Formula 8 | Formula 6 | Formula 6 | —OH | 5.0 ppm (—OH phenolic), 2.0 ppm (—OH aliphatic), 1.9, 6.2, 5.6 ppm (—C(CH$_3$)=CH$_2$), 6.9 ppm (aromatic H) |

Synthetic Example 3

50 mol of the 3,5-dihydroxy benzoic acid was dissolved in acetone using an excessive amount, and agitated, and 100 mol of glycidyl methacrylate was slowly mixed for 1 hour. Next, the mixture that was formed of the compound represented by the following Formula 12 was obtained by purifying the reactant.

[Formula 12]

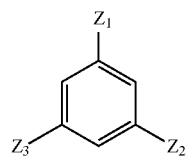

In Formula 12, $Z_1$, $Z_2$, and $Z_3$ are selected from combinations of the following Table 3.

TABLE 3

| Combination | $z_1$ | $z_2$ | $z_3$ | $^1$H NMR |
|---|---|---|---|---|
| 1 | —C(O)OH | Formula 6 | Formula 6 | 11 ppm (—COOH), 2.0 ppm (—OH aliphatic), 1.9, 6.2, 5.6 ppm (—C(CH$_3$)=CH$_2$), 7.2, 6.6 ppm (aromatic H) |
| 2 | Formula 8 | —OH | Formula 6 | 5.0 ppm (—OH phenolic), 2.0 ppm (—OH aliphatic), 1.9, 6.2, 5.6 ppm (—CH=CH$_2$), 7.2, 6.6 ppm (aromatic H) |
| 3 | Formula 8 | Formula 6 | —OH | 5.0 ppm (—OH phenolic), 2.0 ppm (—OH aliphatic), 1.9, 6.2, 5.6 ppm (—CH=CH$_2$), 7.2, 6.6 ppm (aromatic H) |

Synthetic Example 4

50 mol of 1,8,9-trihydroxy anthracene was dissolved in acetone using an excessive amount and agitated, and 100 mol of glycidyl methacrylate was slowly mixed for 1 hour. Next, the mixture that was formed of the compound represented by the following Formula 13 was obtained by purifying the reactant.

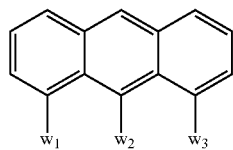

[Formula 13]

In Formula 13, $w_1$, $w_2$ and $w_3$ are selected from combinations of the following Table 4.

TABLE 4

| Combination | $w_1$ | $w_2$ | $w_3$ | $^1$H NMR |
|---|---|---|---|---|
| 1 | —OH | Formula 6 | Formula 6 | 5.0 ppm (—OH phenolic), 2.0 ppm (—OH aliphatic), 1.9, 6.2, 5.6 ppm (—CH=CH$_2$), 7.3, 7.2, 6.6 ppm (aromatic H) |
| 2 | Formula 6 | —OH | Formula 6 | 5.0 ppm (—OH phenolic), 2.0 ppm (—OH aliphatic), 1.9, 6.2, 5.6 ppm (—CH=CH$_2$), 7.3, 7.2, 6.6 ppm (aromatic H) |
| 3 | Formula 6 | Formula 6 | —OH | 5.0 ppm (—OH phenolic), 2.0 ppm (—OH aliphatic), 1.9, 6.2, 5.6 ppm (—CH=CH$_2$), 7.3, 7.2, 6.6 ppm (aromatic H) |

Synthetic Example 5

Synthetic Example 5 was the same as Synthetic Example 1, except that 150 mole of glycidyl methacrylate in Synthetic Example 1 was substituted with 150 mol of glycidyl acrylate. Thereby, the mixture that was formed of the compound represented by the following Formula 10 was obtained. In the following Formula 10, $X_1$, $X_2$, $X_3$, and $X_4$ are selected from combinations of the following Table 5.

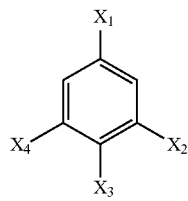

[Formula 10]

TABLE 5

| Combination | $X_1$ | $X_2$ | $X_3$ | $X_4$ | $^1$H NMR |
|---|---|---|---|---|---|
| 1 | —C(O)OH | Formula 7 | Formula 7 | Formula 7 | 11.0 ppm (—COOH), 2.0 ppm (—OH aliphatic), 6.2, 5.6 ppm (—CH=CH$_2$), 7.1 ppm (aromatic H) |
| 2 | Formula 9 | —OH | Formula 7 | Formula 7 | 5.0 ppm (—OH phenolic), 2.0 ppm (—OH aliphatic), 6.2, 5.6 ppm (—CH=CH$_2$), 6.9 ppm (aromatic H) |
| 3 | Formula 9 | Formula 7 | —OH | Formula 7 | 5.0 ppm (—OH phenolic), 2.0 ppm (—OH aliphatic 6.2, 5.6 ppm (—CH=CH$_2$), 6.9 ppm (aromatic H) |
| 4 | Formula 9 | Formula 7 | Formula 7 | —OH | 5.0 ppm (—OH phenolic), 2.0 ppm (—OH aliphatic 6.2, 5.6 ppm (—CH=CH$_2$), 6.9 ppm (aromatic H) |

Synthetic Example 6

Synthetic Example 6 was the same as Synthetic Example 2, except that 150 mole of glycidyl methacrylate in Synthetic Example 2 was substituted with 150 mol of glycidyl acrylate. Thereby, the mixture that was formed of the compound represented by the following Formula 10 was obtained. In the following Formula 11, $y_1$, $y_2$, $y_3$, and $y_4$ are selected from combinations of the following Table 6.

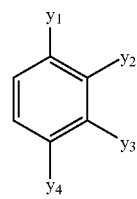

[Formula 11]

TABLE 6

| Combination | $y_1$ | $y_2$ | $y_3$ | $y_4$ | $^1$H NMR |
|---|---|---|---|---|---|
| 1 | —C(O)OH | Formula 7 | Formula 7 | Formula 7 | 11.0 ppm (—COOH), 2.0 ppm (—OH aliphatic), 6.2, 5.6 ppm (—CH=CH$_2$), 7.1 ppm (aromatic H) |
| 2 | Formula 9 | —OH | Formula 7 | Formula 7 | 5.0 ppm (—OH phenolic), 2.0 ppm (—OH aliphatic), 6.2, 5.6 ppm (—CH=CH$_2$), 6.9 ppm (aromatic H) |
| 3 | Formula 9 | Formula 7 | —OH | Formula 7 | 5.0 ppm (—OH phenolic), 2.0 ppm (—OH aliphatic), 6.2, 5.6 ppm |

TABLE 6-continued

| Combination | $y_1$ | $y_2$ | $y_3$ | $y_4$ | $^1$H NMR |
|---|---|---|---|---|---|
| 4 | Formula 9 | Formula 7 | Formula 7 | —OH | (—CH=CH$_2$), 6.9 ppm (aromatic H) 5.0 ppm (—OH phenolic), 2.0 ppm (—OH aliphatic), 6.2, 5.6 ppm (—CH=CH$_2$), 6.9 ppm (aromatic H) |

Synthetic Example 7

Synthetic Example 7 was the same as Synthetic Example 3, except that 100 mole of glycidyl methacrylate in Synthetic Example 3 was substituted with 150 mol of glycidyl acrylate. Thereby, the mixture that was formed of the compound represented by the following Formula 12 was obtained. In the following Formula 12, $Z_1$, $Z_2$, and $Z_3$ are selected from combinations of the following Table 7.

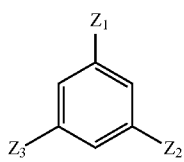

[Formula 12]

TABLE 7

| Combination | $z_1$ | $z_2$ | $z_3$ | $^1$H NMR |
|---|---|---|---|---|
| 1 | —C(O)OH | Formula 7 | Formula 7 | 11 ppm (—COOH), 2.0 ppm (—OH aliphatic), 6.2, 5.6 ppm (—CH=CH$_2$), 7.2, 6.6 ppm (aromatic H) |
| 2 | Formula 9 | —OH | Formula 7 | 5.0 ppm (—OH phenolic), 2.0 ppm (—OH aliphatic), 6.2, 5.6 ppm (—CH=CH$_2$), 7.2, 6.6 ppm (aromatic H) |
| 3 | Formula 9 | Formula 7 | —OH | 5.0 ppm (—OH phenolic), 2.0 ppm (—OH aliphatic), 6.2, 5.6 ppm (—CH=CH$_2$), 7.2, 6.6 ppm (aromatic H) |

Synthetic Example 8

Synthetic Example 8 was the same as Synthetic Example 4, except that 100 mole of glycidyl methacrylate in Synthetic Example 4 was substituted with 150 mol of glycidyl acrylate. Thereby, the mixture that was formed of the compound represented by the following Formula 13 was obtained. In the following Formula 13, $w_1$, $w_2$ and $w_3$ are selected from combinations of the following Table 8.

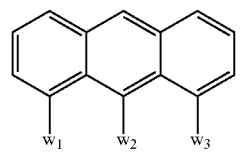

[Formula 13]

TABLE 8

| Combination | $w_1$ | $w_2$ | $w_3$ | $^1$H NMR |
|---|---|---|---|---|
| 1 | —OH | Formula 7 | Formula 7 | 5.0 ppm (—OH phenolic), 2.0 ppm (—OH aliphatic), 1.9, 6.2, 5.6 ppm (—CH=CH$_2$), 7.3, 7.2, 6.6 ppm (aromatic H) |
| 2 | Formula 7 | —OH | Formula 7 | 5.0 ppm (—OH phenolic), 2.0 ppm (—OH aliphatic), 1.9, 6.2, 5.6 ppm (—CH=CH$_2$), 7.3, 7.2, 6.6 ppm (aromatic H) |
| 3 | Formula 7 | Formula 7 | —OH | 5.0 ppm (—OH phenolic), 2.0 ppm (—OH aliphatic), 1.9, 6.2, 5.6 ppm (—CH=CH$_2$), 7.3, 7.2, 6.6 ppm (aromatic H) |

Example 1

The following photosensitive composition was manufactured in order to confirm the effect of the exemplary embodiment of the present invention. 8 parts by weight of the binder BzMA/MAA (molar ratio: 70/30, Mw: 24,000) formed of the alkali soluble resin, 16 parts by weight of the dipentaerythritol hexaacrylate compound as the crosslinking compound, 1 part by weight of Irgacure 369(2-benzyl-2-dimethylamino-1-(4-morpholinophenyl)-butane-1-one) manufactured by Ciba-Geigy Co., Ltd. as the photopolymerization initiator, 0.8 parts by weight (5% of the crosslinking compound) of the acrylate-based compound provided in Synthetic Example 1, and PGMEA that was the organic solvent were added so that the total content was 100 parts by weight, and mixed by using the shaker for 3 hours to form the solution, and the solution was filtered with the filter of 5 microns.

After the uniform thin film was formed by coating the photosensitive composition by the method such as spin coating, slit coating, dip coating, or doctor blading, the solvent was volatilized by performing the prebake process at 100° C. for 200 sec. The thickness of the dried thin film was about 4 microns. Next, the thin film was exposed under the high voltage mercury lamp by using the circular independent pattern type photomask having the diameter of 30 microns. The exposed substrate was developed by the spray manner in the 0.04% KOH aqueous solution at the temperature of 25° C., washed with pure water, and dried by air blowing.

Example 2

The same manner as Example 1 was performed, except that 1.6 parts by weight (10% of the crosslinking compound) of the acrylate-based compound was used instead of 0.8 parts by weight (5% of the crosslinking compound) of the acrylate-based compound manufactured in Synthetic Example 1 in Example 1.

Example 3

The same manner as Example 1 was performed, except that 2.4 parts by weight (15% of the crosslinking compound) of the acrylate-based compound was used instead of 0.8 parts by weight (5% of the crosslinking compound) of the acrylate-based compound manufactured in Synthetic Example 1 in Example 1.

Example 4

The same manner as Example 1 was performed, except that 3.2 parts by weight (20% of the crosslinking compound) of the acrylate-based compound was used instead of 0.8 parts by weight (5% of the crosslinking compound) of the acrylate-based compound manufactured in Synthetic Example 1 in Example 1.

Example 5

The same manner as Example 1 was performed, except that 4.0 parts by weight (25% of the crosslinking compound) of the acrylate-based compound was used instead of 0.8 parts by weight (5% of the crosslinking compound) of the acrylate-based compound manufactured in Synthetic Example 1 in Example 1.

Example 6

The same manner as Example 1 was performed, except that 0.8 parts by weight (5% of the crosslinking compound) of the acrylate-based compound manufactured in Synthetic Example 2 was used instead of 0.8 parts by weight (5% of the crosslinking compound) of the acrylate-based compound manufactured in Synthetic Example 1 in Example 1.

Example 7

The same manner as Example 1 was performed, except that 1.6 parts by weight (10% of the crosslinking compound) of the acrylate-based compound manufactured in Synthetic Example 2 was used instead of 0.8 parts by weight (5% of the crosslinking compound) of the acrylate-based compound manufactured in Synthetic Example 1 in Example 1.

Example 8

The same manner as Example 1 was performed, except that 2.4 parts by weight (15% of the crosslinking compound) of the acrylate-based compound manufactured in Synthetic Example 2 was used instead of 0.8 parts by weight (5% of the crosslinking compound) of the acrylate-based compound manufactured in Synthetic Example 1 in Example 1.

Example 9

The same manner as Example 1 was performed, except that 3.2 parts by weight (20% of the crosslinking compound) of the acrylate-based compound manufactured in Synthetic Example 2 was used instead of 0.8 parts by weight (5% of the crosslinking compound) of the acrylate-based compound manufactured in Synthetic Example 1 in Example 1.

Example 10

The same manner as Example 1 was performed, except that 4.0 parts by weight (25% of the crosslinking compound) of the acrylate-based compound manufactured in Synthetic Example 2 was used instead of 0.8 parts by weight (5% of the crosslinking compound) of the acrylate-based compound manufactured in Synthetic Example 1 in Example 1.

Example 11

The same manner as Example 1 was performed, except that 0.8 parts by weight (5% of the crosslinking compound) of the acrylate-based compound manufactured in Synthetic Example 3 was used instead of 0.8 parts by weight (5% of the crosslinking compound) of the acrylate-based compound manufactured in Synthetic Example 1 in Example 1.

Example 12

The same manner as Example 1 was performed, except that 1.6 parts by weight (10% of the crosslinking compound) of the acrylate-based compound manufactured in Synthetic Example 3 was used instead of 0.8 parts by weight (5% of the crosslinking compound) of the acrylate-based compound manufactured in Synthetic Example 1 in Example 1.

Example 13

The same manner as Example 1 was performed, except that 2.4 parts by weight (15% of the crosslinking compound) of the acrylate-based compound manufactured in Synthetic Example 3 was used instead of 0.8 parts by weight (5% of the crosslinking compound) of the acrylate-based compound manufactured in Synthetic Example 1 in Example 1.

Example 14

The same manner as Example 1 was performed, except that 3.2 parts by weight (20% of the crosslinking compound) of the acrylate-based compound manufactured in Synthetic Example 3 was used instead of 0.8 parts by weight (5% of the crosslinking compound) of the acrylate-based compound manufactured in Synthetic Example 1 in Example 1.

Example 15

The same manner as Example 1 was performed, except that 4.0 parts by weight (25% of the crosslinking compound) of the acrylate-based compound manufactured in Synthetic Example 3 was used instead of 0.8 parts by weight (5% of the crosslinking compound) of the acrylate-based compound manufactured in Synthetic Example 1 in Example 1.

Example 16

The same manner as Example 1 was performed, except that 0.8 parts by weight (5% of the crosslinking compound) of the acrylate-based compound manufactured in Synthetic Example 4 was used instead of 0.8 parts by weight (5% of the crosslinking compound) of the acrylate-based compound manufactured in Synthetic Example 1 in Example 1.

Example 17

The same manner as Example 1 was performed, except that 1.6 parts by weight (10% of the crosslinking compound) of the acrylate-based compound manufactured in Synthetic Example 4 was used instead of 0.8 parts by weight (5% of the crosslinking compound) of the acrylate-based compound manufactured in Synthetic Example 1 in Example 1.

Example 18

The same manner as Example 1 was performed, except that 2.4 parts by weight (15% of the crosslinking compound) of

Example 19

The same manner as Example 1 was performed, except that 3.2 parts by weight (20% of the crosslinking compound) of the acrylate-based compound manufactured in Synthetic Example 4 was used instead of 0.8 parts by weight (5% of the crosslinking compound) of the acrylate-based compound manufactured in Synthetic Example 1 in Example 1.

Example 20

The same manner as Example 1 was performed, except that 4.0 parts by weight (25% of the crosslinking compound) of the acrylate-based compound manufactured in Synthetic Example 4 was used instead of 0.8 parts by weight (5% of the crosslinking compound) of the acrylate-based compound manufactured in Synthetic Example 1 in Example 1.

Example 21

The same manner as Example 1 was performed, except that 0.8 parts by weight (5% of the crosslinking compound) of the acrylate-based compound manufactured in Synthetic Example 5 was used instead of 0.8 parts by weight (5% of the crosslinking compound) of the acrylate-based compound manufactured in Synthetic Example 1 in Example 1.

Example 22

The same manner as Example 1 was performed, except that 1.6 parts by weight (10% of the crosslinking compound) of the acrylate-based compound manufactured in Synthetic Example 5 was used instead of 0.8 parts by weight (5% of the crosslinking compound) of the acrylate-based compound manufactured in Synthetic Example 1 in Example 1.

Example 23

The same manner as Example 1 was performed, except that 2.4 parts by weight (15% of the crosslinking compound) of the acrylate-based compound manufactured in Synthetic Example 5 was used instead of 0.8 parts by weight (5% of the crosslinking compound) of the acrylate-based compound manufactured in Synthetic Example 1 in Example 1.

Example 24

The same manner as Example 1 was performed, except that 3.2 parts by weight (20% of the crosslinking compound) of the acrylate-based compound manufactured in Synthetic Example 5 was used instead of 0.8 parts by weight (5% of the crosslinking compound) of the acrylate-based compound manufactured in Synthetic Example 1 in Example 1.

Example 25

The same manner as Example 1 was performed, except that 4.0 parts by weight (25% of the crosslinking compound) of the acrylate-based compound manufactured in Synthetic Example 5 was used instead of 0.8 parts by weight (5% of the crosslinking compound) of the acrylate-based compound manufactured in Synthetic Example 1 in Example 1.

Example 26

The same manner as Example 1 was performed, except that 0.8 parts by weight (5% of the crosslinking compound) of the acrylate-based compound manufactured in Synthetic Example 6 was used instead of 0.8 parts by weight (5% of the crosslinking compound) of the acrylate-based compound manufactured in Synthetic Example 1 in Example 1.

Example 27

The same manner as Example 1 was performed, except that 1.6 parts by weight (10% of the crosslinking compound) of the acrylate-based compound manufactured in Synthetic Example 6 was used instead of 0.8 parts by weight (5% of the crosslinking compound) of the acrylate-based compound manufactured in Synthetic Example 1 in Example 1.

Example 28

The same manner as Example 1 was performed, except that 2.4 parts by weight (15% of the crosslinking compound) of the acrylate-based compound manufactured in Synthetic Example 6 was used instead of 0.8 parts by weight (5% of the crosslinking compound) of the acrylate-based compound manufactured in Synthetic Example 1 in Example 1.

Example 29

The same manner as Example 1 was performed, except that 3.2 parts by weight (20% of the crosslinking compound) of the acrylate-based compound manufactured in Synthetic Example 6 was used instead of 0.8 parts by weight (5% of the crosslinking compound) of the acrylate-based compound manufactured in Synthetic Example 1 in Example 1.

Example 30

The same manner as Example 1 was performed, except that 4.0 parts by weight (25% of the crosslinking compound) of the acrylate-based compound manufactured in Synthetic Example 6 was used instead of 0.8 parts by weight (5% of the crosslinking compound) of the acrylate-based compound manufactured in Synthetic Example 1 in Example 1.

Example 31

The same manner as Example 1 was performed, except that 0.8 parts by weight (5% of the crosslinking compound) of the acrylate-based compound manufactured in Synthetic Example 4 was used instead of 0.8 parts by weight (5% of the crosslinking compound) of the acrylate-based compound manufactured in Synthetic Example 1 in Example 1.

Example 32

The same manner as Example 1 was performed, except that 1.6 parts by weight (10% of the crosslinking compound) of the acrylate-based compound manufactured in Synthetic Example 4 was used instead of 0.8 parts by weight (5% of the crosslinking compound) of the acrylate-based compound manufactured in Synthetic Example 1 in Example 1.

Example 33

The same manner as Example 1 was performed, except that 2.4 parts by weight (15% of the crosslinking compound) of the acrylate-based compound manufactured in Synthetic Example 4 was used instead of 0.8 parts by weight (5% of the crosslinking compound) of the acrylate-based compound manufactured in Synthetic Example 1 in Example 1.

Example 34

The same manner as Example 1 was performed, except that 3.2 parts by weight (20% of the crosslinking compound) of the acrylate-based compound manufactured in Synthetic Example 4 was used instead of 0.8 parts by weight (5% of the crosslinking compound) of the acrylate-based compound manufactured in Synthetic Example 1 in Example 1.

Example 35

The same manner as Example 1 was performed, except that 4.0 parts by weight (25% of the crosslinking compound) of the acrylate-based compound manufactured in Synthetic Example 4 was used instead of 0.8 parts by weight (5% of the crosslinking compound) of the acrylate-based compound manufactured in Synthetic Example 1 in Example 1.

Example 36

The same manner as Example 1 was performed, except that 0.8 parts by weight (5% of the crosslinking compound) of the acrylate-based compound manufactured in Synthetic Example 4 was used instead of 0.8 parts by weight (5% of the crosslinking compound) of the acrylate-based compound manufactured in Synthetic Example 1 in Example 1.

Example 37

The same manner as Example 1 was performed, except that 1.6 parts by weight (10% of the crosslinking compound) of the acrylate-based compound manufactured in Synthetic Example 4 was used instead of 0.8 parts by weight (5% of the crosslinking compound) of the acrylate-based compound manufactured in Synthetic Example 1 in Example 1.

Example 38

The same manner as Example 1 was performed, except that 2.4 parts by weight (15% of the crosslinking compound) of the acrylate-based compound manufactured in Synthetic Example 4 was used instead of 0.8 parts by weight (5% of the crosslinking compound) of the acrylate-based compound manufactured in Synthetic Example 1 in Example 1.

Example 39

The same manner as Example 1 was performed, except that 3.2 parts by weight (20% of the crosslinking compound) of the acrylate-based compound manufactured in Synthetic Example 4 was used instead of 0.8 parts by weight (5% of the crosslinking compound) of the acrylate-based compound manufactured in Synthetic Example 1 in Example 1.

Example 40

The same manner as Example 1 was performed, except that 4.0 parts by weight (25% of the crosslinking compound) of the acrylate-based compound manufactured in Synthetic Example 4 was used instead of 0.8 parts by weight (5% of the crosslinking compound) of the acrylate-based compound manufactured in Synthetic Example 1 in Example 1.

Example 41

The same manner as Example 1 was performed, except that 0.5 parts by weight (3% of the crosslinking compound) of the acrylate-based compound was used instead of 0.8 parts by weight (5% of the crosslinking compound) of the acrylate-based compound manufactured in Synthetic Example 1 in Example 1.

Example 42

The same manner as Example 1 was performed, except that 5.0 parts by weight (31% of the crosslinking compound) of the acrylate-based compound was used instead of 0.8 parts by weight (5% of the crosslinking compound) of the acrylate-based compound manufactured in Synthetic Example 1 in Example 1.

Example 43

The same manner as Example 1 was performed, except that 0.5 parts by weight (3% of the crosslinking compound) of the acrylate-based compound manufactured in Synthetic Example 2 was used instead of 0.8 parts by weight (5% of the crosslinking compound) of the acrylate-based compound manufactured in Synthetic Example 1 in Example 1.

Example 44

The same manner as Example 1 was performed, except that 5.0 parts by weight (31% of the crosslinking compound) of the acrylate-based compound manufactured in Synthetic Example 2 was used instead of 0.8 parts by weight (5% of the crosslinking compound) of the acrylate-based compound manufactured in Synthetic Example 1 in Example 1.

Example 45

The same manner as Example 1 was performed, except that 0.5 parts by weight (3% of the crosslinking compound) of the acrylate-based compound manufactured in Synthetic Example 3 was used instead of 0.8 parts by weight (5% of the crosslinking compound) of the acrylate-based compound manufactured in Synthetic Example 1 in Example 1.

Example 46

The same manner as Example 1 was performed, except that 5.0 parts by weight (31% of the crosslinking compound) of the acrylate-based compound manufactured in Synthetic Example 3 was used instead of 0.8 parts by weight (5% of the crosslinking compound) of the acrylate-based compound manufactured in Synthetic Example 1 in Example 1.

Example 47

The same manner as Example 1 was performed, except that 0.5 parts by weight (3% of the crosslinking compound) of the acrylate-based compound manufactured in Synthetic Example 4 was used instead of 0.8 parts by weight (5% of the crosslinking compound) of the acrylate-based compound manufactured in Synthetic Example 1 in Example 1.

Example 48

The same manner as Example 1 was performed, except that 5.0 parts by weight (31% of the crosslinking compound) of the acrylate-based compound manufactured in Synthetic Example 4 was used instead of 0.8 parts by weight (5% of the crosslinking compound) of the acrylate-based compound manufactured in Synthetic Example 1 in Example 1.

Example 49

The same manner as Example 1 was performed, except that 0.5 parts by weight (3% of the crosslinking compound) of the acrylate-based compound manufactured in Synthetic Example 5 was used instead of 0.8 parts by weight (5% of the crosslinking compound) of the acrylate-based compound manufactured in Synthetic Example 1 in Example 1.

Example 50

The same manner as Example 1 was performed, except that 5.0 parts by weight (31% of the crosslinking compound) of the acrylate-based compound manufactured in Synthetic Example 5 was used instead of 0.8 parts by weight (5% of the crosslinking compound) of the acrylate-based compound manufactured in Synthetic Example 1 in Example 1.

Example 51

The same manner as Example 1 was performed, except that 0.5 parts by weight (3% of the crosslinking compound) of the acrylate-based compound manufactured in Synthetic Example 6 was used instead of 0.8 parts by weight (5% of the crosslinking compound) of the acrylate-based compound manufactured in Synthetic Example 1 in Example 1.

Example 52

The same manner as Example 1 was performed, except that 5.0 parts by weight (31% of the crosslinking compound) of the acrylate-based compound manufactured in Synthetic Example 6 was used instead of 0.8 parts by weight (5% of the crosslinking compound) of the acrylate-based compound manufactured in Synthetic Example 1 in Example 1.

Example 53

The same manner as Example 1 was performed, except that 0.5 parts by weight (3% of the crosslinking compound) of the acrylate-based compound manufactured in Synthetic Example 7 was used instead of 0.8 parts by weight (5% of the crosslinking compound) of the acrylate-based compound manufactured in Synthetic Example 1 in Example 1.

Example 54

The same manner as Example 1 was performed, except that 5.0 parts by weight (31% of the crosslinking compound) of the acrylate-based compound manufactured in Synthetic Example 7 was used instead of 0.8 parts by weight (5% of the crosslinking compound) of the acrylate-based compound manufactured in Synthetic Example 1 in Example 1.

Example 55

The same manner as Example 1 was performed, except that 0.5 parts by weight (3% of the crosslinking compound) of the acrylate-based compound manufactured in Synthetic Example 8 was used instead of 0.8 parts by weight (5% of the crosslinking compound) of the acrylate-based compound manufactured in Synthetic Example 1 in Example 1.

Example 56

The same manner as Example 1 was performed, except that 5.0 parts by weight (31% of the crosslinking compound) of the acrylate-based compound manufactured in Synthetic Example 8 was used instead of 0.8 parts by weight (5% of the crosslinking compound) of the acrylate-based compound manufactured in Synthetic Example 1 in Example 1.

Comparative Example 1

The same manner as Example 1 was performed, except that 0.8 parts by weight (5% of the crosslinking compound) of the acrylate-based compound represented by the following Formula 14 was used instead of 0.5 parts by weight (3% of the crosslinking compound) of the acrylate-based compound manufactured in Synthetic Example 1 in Example 1.

[Formula 14]

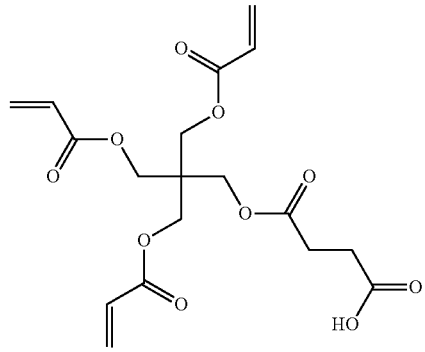

Comparative Example 2

The same manner as Example 1 was performed, except that 1.6 parts by weight (10% of the crosslinking compound) of the acrylate-based compound represented by Formula 14 was used instead of 0.8 parts by weight (5% of the crosslinking compound) of the acrylate-based compound manufactured in Synthetic Example 1 in Example 1.

Comparative Example 3

The same manner as Example 1 was performed, except that 2.4 parts by weight (15% of the crosslinking compound) of the acrylate-based compound represented by Formula 14 was used instead of 0.8 parts by weight (5% of the crosslinking compound) of the acrylate-based compound manufactured in Synthetic Example 1 in Example 1.

Comparative Example 4

The same manner as Example 1 was performed, except that 3.2 parts by weight (20% of the crosslinking compound) of the acrylate-based compound represented by Formula 14 was used instead of 0.8 parts by weight (5% of the crosslinking compound) of the acrylate-based compound manufactured in Synthetic Example 1 in Example 1.

Comparative Example 5

The same manner as Example 1 was performed, except that 4.0 parts by weight (25% of the crosslinking compound) of the acrylate-based compound represented by Formula 14 was used instead of 0.8 parts by weight (5% of the crosslinking compound) of the acrylate-based compound manufactured in Synthetic Example 1 in Example 1.

Comparative Example 6

The same manner as Example 1 was performed, except that 0.8 parts by weight (5% of the crosslinking compound) of the acrylate-based compound manufactured in Synthetic Example 1 was not used in Example 1.

Comparative Example 7

The same manner as Example 1 was performed, except that 8 parts by weight of the binder BzMA/MAA (molar ratio: 70/30, Mw: 24,000) formed of the alkali soluble resin was not used in Example 1.

Comparative Example 8

The same manner as Example 6 was performed, except that 8 parts by weight of the binder BzMA/MAA (molar ratio: 70/30, Mw: 24,000) formed of the alkali soluble resin was not used in Example 6.

Comparative Example 9

The same manner as Example 11 was performed, except that 8 parts by weight of the binder BzMA/MAA (molar ratio: 70/30, Mw: 24,000) formed of the alkali soluble resin was not used in Example 11.

Comparative Example 10

The same manner as Example 16 was performed, except that 8 parts by weight of the binder BzMA/MAA (molar ratio: 70/30, Mw: 24,000) formed of the alkali soluble resin was not used in Example 16.

Comparative Example 11

The same manner as Example 21 was performed, except that 8 parts by weight of the binder BzMA/MAA (molar ratio: 70/30, Mw: 24,000) formed of the alkali soluble resin was not used in Example 21.

Comparative Example 12

The same manner as Example 26 was performed, except that 8 parts by weight of the binder BzMA/MAA (molar ratio: 70/30, Mw: 24,000) formed of the alkali soluble resin was not used in Example 26.

Comparative Example 13

The same manner as Example 31 was performed, except that 8 parts by weight of the binder BzMA/MAA (molar ratio: 70/30, Mw: 24,000) formed of the alkali soluble resin was not used in Example 31.

Comparative Example 14

The same manner as Example 36 was performed, except that 8 parts by weight of the binder BzMA/MAA (molar ratio: 70/30, Mw: 24,000) formed of the alkali soluble resin was not used in Example 36.

Test Example 1

Test of the Photosensitivity and Developing Property

In order to confirm photosensitivity by using the photosensitive compositions obtained in Examples and Comparative Examples, the experiment was performed while controlling the exposure amount when exposure was performed under the high voltage mercury lamp, and the exposure amount that did not increase the thickness of the pattern anymore after the final process was performed was determined as the standard. When the exposure amount is decreased, the sensitivity may be excellent. Light of entire wavelength range emitted from the high voltage mercury lamp as the light source was used without the filter for a specific wavelength, and the measurement was performed at 365 nm (I-ray) with respect to the exposure amount.

In the above experiment, the experiment was performed while the developing time was changed in order to measure the developing time. The developing times were compared to each other on the basis of the EBR (Edge-bead Remove) time at which the thin film of the edge of the substrate was completely removed. When the time is short, the developing property is excellent, and the effect intended in the present invention may be exhibited.

The experimental results according to Examples 1 to 56 and Comparative Examples 1 to 6 are described in the following Table 9. Comparative Example 6 as the standard experiment is the case where no acrylate-based compound was used. From the comparison therewith, it can be seen that in all the Examples, the EBR time is shortened according to the content of the acrylate-based compound. In the case where the addition amount was less than 25% on the basis of the crosslinking agent, the addition amount did not affect the sensitivity that was the criterion of the photosensitivity.

TABLE 9

| | Content of the acrylate-based compound | | | | |
| --- | --- | --- | --- | --- | --- |
| | Acrylate-based compound | Relative amount on the basis of the crosslinking compound | Weight ratio | Photosensitivity (sensitivity) (mJ/cm$^2$) | EBR Time (sec) |
| Example 1 | Synthetic Example 1 | 5% | 0.8 | 210 | 48 |
| Example 2 | Synthetic Example 1 | 10% | 1.6 | 210 | 45 |
| Example 3 | Synthetic Example 1 | 15% | 2.4 | 210 | 43 |
| Example 4 | Synthetic Example 1 | 20% | 3.2 | 210 | 40 |
| Example 5 | Synthetic Example 1 | 25% | 4 | 240 | 30 |
| Example 6 | Synthetic Example 2 | 5% | 0.8 | 210 | 48 |
| Example 7 | Synthetic Example 2 | 10% | 1.6 | 210 | 45 |
| Example 8 | Synthetic Example 2 | 15% | 2.4 | 210 | 43 |
| Example 9 | Synthetic Example 2 | 20% | 3.2 | 210 | 40 |

TABLE 9-continued

Content of the acrylate-based compound

| | Acrylate-based compound | Relative amount on the basis of the crosslinking compound | Weight ratio | Photosensitivity (sensitivity) (mJ/cm$^2$) | EBR Time (sec) |
|---|---|---|---|---|---|
| Example 10 | Synthetic Example 2 | 25% | 4 | 230 | 30 |
| Example 11 | Synthetic Example 3 | 5% | 0.8 | 210 | 45 |
| Example 12 | Synthetic Example 3 | 10% | 1.6 | 210 | 41 |
| Example 13 | Synthetic Example 3 | 15% | 2.4 | 210 | 36 |
| Example 14 | Synthetic Example 3 | 20% | 3.2 | 210 | 30 |
| Example 15 | Synthetic Example 3 | 25% | 4 | 270 | 25 |
| Example 16 | Synthetic Example 4 | 5% | 0.8 | 210 | 46 |
| Example 17 | Synthetic Example 4 | 10% | 1.6 | 210 | 43 |
| Example 18 | Synthetic Example 4 | 15% | 2.4 | 210 | 38 |
| Example 19 | Synthetic Example 4 | 20% | 3.2 | 210 | 33 |
| Example 20 | Synthetic Example 4 | 25% | 4 | 240 | 29 |
| Example 21 | Synthetic Example 5 | 5% | 0.8 | 210 | 48 |
| Example 22 | Synthetic Example 5 | 10% | 1.6 | 210 | 45 |
| Example 23 | Synthetic Example 5 | 15% | 2.4 | 210 | 43 |
| Example 24 | Synthetic Example 5 | 20% | 3.2 | 210 | 40 |
| Example 25 | Synthetic Example 5 | 25% | 4 | 240 | 30 |
| Example 26 | Synthetic Example 6 | 5% | 0.8 | 210 | 48 |
| Example 27 | Synthetic Example 6 | 10% | 1.6 | 210 | 45 |
| Example 28 | Synthetic Example 6 | 15% | 2.4 | 210 | 43 |
| Example 29 | Synthetic Example 6 | 20% | 3.2 | 210 | 40 |
| Example 30 | Synthetic Example 6 | 25% | 4 | 230 | 30 |
| Example 31 | Synthetic Example 7 | 5% | 0.8 | 210 | 45 |
| Example 32 | Synthetic Example 7 | 10% | 1.6 | 210 | 41 |
| Example 33 | Synthetic Example 7 | 15% | 2.4 | 210 | 36 |
| Example 34 | Synthetic Example 7 | 20% | 3.2 | 210 | 30 |
| Example 35 | Synthetic Example 7 | 25% | 4 | 270 | 25 |
| Example 36 | Synthetic Example 8 | 5% | 0.8 | 210 | 46 |
| Example 37 | Synthetic Example 8 | 10% | 1.6 | 210 | 43 |
| Example 38 | Synthetic Example 8 | 15% | 2.4 | 210 | 38 |
| Example 39 | Synthetic Example 8 | 20% | 3.2 | 210 | 33 |
| Example 40 | Synthetic Example 8 | 25% | 4 | 240 | 29 |
| Example 41 | Synthetic Example 1 | 3% | 0.5 | 210 | 49 |
| Example 42 | Synthetic Example 1 | 31% | 5 | 270 | 24 |
| Example 43 | Synthetic Example 2 | 3% | 0.5 | 210 | 50 |
| Example 44 | Synthetic Example 2 | 31% | 5 | 290 | 23 |
| Example 45 | Synthetic Example 3 | 3% | 0.5 | 210 | 50 |
| Example 46 | Synthetic Example 3 | 31% | 5 | 280 | 20 |
| Example 47 | Synthetic Example 4 | 3% | 0.5 | 210 | 50 |
| Example 48 | Synthetic Example 4 | 31% | 5 | 270 | 20 |
| Example 49 | Synthetic Example 5 | 3% | 0.5 | 210 | 49 |
| Example 50 | Synthetic Example 5 | 31% | 5 | 280 | 20 |
| Example 51 | Synthetic Example 6 | 3% | 0.5 | 210 | 50 |
| Example 52 | Synthetic Example 6 | 31% | 5 | 270 | 17 |
| Example 53 | Synthetic Example 7 | 3% | 0.5 | 210 | 50 |
| Example 54 | Synthetic Example 7 | 31% | 5 | 290 | 22 |
| Example 55 | Synthetic Example 8 | 3% | 0.5 | 210 | 49 |
| Example 56 | Synthetic Example 8 | 31% | 5 | 280 | 19 |
| Comparative Example 1 | Formula 14 | 5% | 0.8 | 240 | 45 |
| Comparative Example 2 | Formula 14 | 10% | 1.6 | 270 | 40 |
| Comparative Example 3 | Formula 14 | 15% | 2.4 | 300 | 35 |
| Comparative Example 4 | Formula 14 | 20% | 3.2 | 310 | 31 |
| Comparative Example 5 | Formula 14 | 25% | 4 | 340 | 26 |
| Comparative Example 6 | — | — | — | 210 | 50 |

On the other hand, Comparative Examples 1 to 5 represent the case where the structure of the central molecule is formed of aliphatics and the organic acid and acrylate are mixed with each other. Unlike Examples 1 to 56, a phenomenon that the photosensitivity is deteriorated in proportion to the used amount may be observed. This is because in the case where the central structure is formed of planar aromatics like the molecules manufactured in Synthetic Examples 1 to 8, reactivity of acrylate is improved.

Test Example 2

Test of the Viscosity and Patterning

In order to confirm the viscosity of the photosensitive composition obtained in Examples and Comparative Examples, the experiment using the capillary viscometer was performed. The viscosity was measured by the ViscoClock manufactured by Schott, Co., Ltd.

In order to confirm the patterning effect, after developing was performed by using the compositions of the Examples and Comparative Examples, whether the pattern was formed or not was observed by using the scanning electron microscope.

The experimental results according to Examples 1 to 56 and Comparative Examples 1 to 14 are described in the following Table 10.

Comparative Examples 7 to 16 as the standard experiment are the case where the binder is not used. In the case where the binder was used, since the viscosity was controlled to 11 to 20 cSt, the thin film could be formed. However, in the case where the binder was not used, since the viscosity was 2.5 cSt, it was difficult to control the viscosity and the thin film could not be formed.

Figure 2:
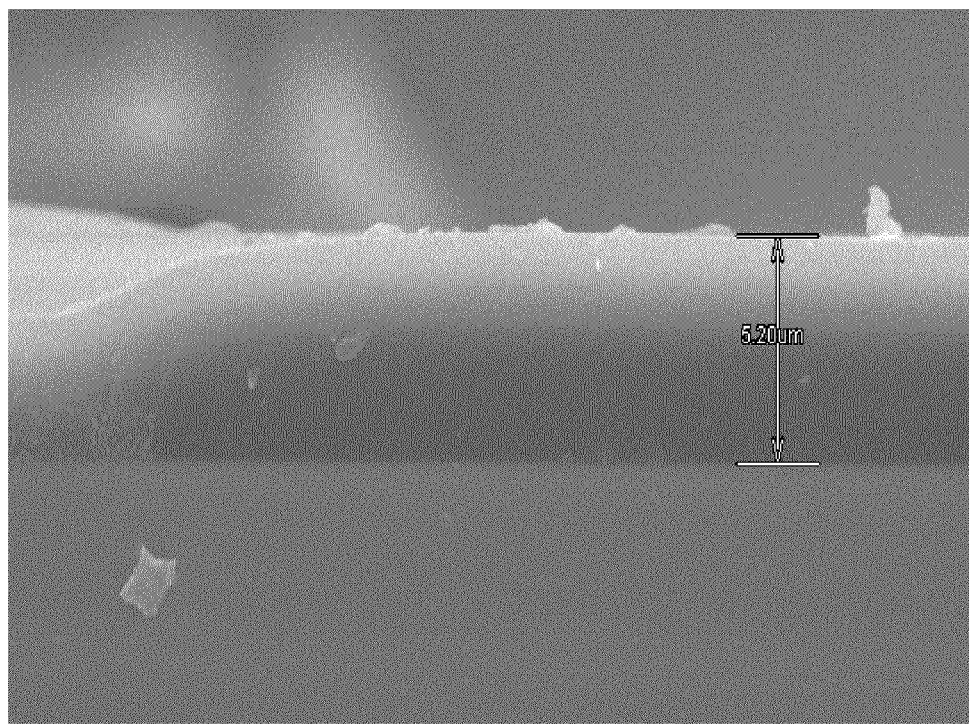
FIG. 2 illustrates results of observing whether a pattern is formed or not by a scanning electron microscope after developing is performed by using a composition of Comparative Example 2.

In the case where the binder was used, the patterning was possible, but in the case where the binder was not used, the patterning was impossible. After developing was performed by using the composition of Example 1, whether the pattern was formed or not was observed by the scanning electron microscope, and the results are illustrated in FIG. 1. After developing was performed by using the composition of Comparative Example 7, whether the pattern was formed or not was observed by the scanning electron microscope, and the results are illustrated in FIG. 2. FIG. 2 illustrates that it is impossible to form the pattern. In the patterning test of the following Table 10, O means that it is possible to implement the patterning, and X means that it is impossible to implement patterning.

TABLE 10

| Classification | Acrylate-based compound | Content of the acrylate-based compound (weight ratio) | Use content of the binder (weight ratio) | Viscosity (cSt) | Patterning experiment |
|---|---|---|---|---|---|
| Example 1 | Synthetic Example 1 | 0.8 | 8 | 12 | O |
| Example 2 | Synthetic Example 1 | 1.6 | 8 | 13 | O |
| Example 3 | Synthetic Example 1 | 2.4 | 8 | 14 | O |
| Example 4 | Synthetic Example 1 | 3.2 | 8 | 16 | O |
| Example 5 | Synthetic Example 1 | 4 | 8 | 18 | O |
| Example 6 | Synthetic Example 2 | 0.8 | 8 | 12 | O |
| Example 7 | Synthetic Example 2 | 1.6 | 8 | 13 | O |
| Example 8 | Synthetic Example 2 | 2.4 | 8 | 14 | O |
| Example 9 | Synthetic Example 2 | 3.2 | 8 | 16 | O |
| Example 10 | Synthetic Example 2 | 4 | 8 | 18 | O |
| Example 11 | Synthetic Example 3 | 0.8 | 8 | 12 | O |
| Example 12 | Synthetic Example 3 | 1.6 | 8 | 13 | O |
| Example 13 | Synthetic Example 3 | 2.4 | 8 | 14 | O |
| Example 14 | Synthetic Example 3 | 3.2 | 8 | 16 | O |
| Example 15 | Synthetic Example 3 | 4 | 8 | 18 | O |
| Example 16 | Synthetic Example 4 | 0.8 | 8 | 12 | O |
| Example 17 | Synthetic Example 4 | 1.6 | 8 | 13 | O |
| Example 18 | Synthetic Example 4 | 2.4 | 8 | 14 | O |
| Example 19 | Synthetic Example 4 | 3.2 | 8 | 16 | O |
| Example 20 | Synthetic Example 4 | 4 | 8 | 18 | O |
| Example 21 | Synthetic Example 5 | 0.8 | 8 | 12 | O |
| Example 22 | Synthetic Example 5 | 1.6 | 8 | 13 | O |
| Example 23 | Synthetic Example 5 | 2.4 | 8 | 14 | O |
| Example 24 | Synthetic Example 5 | 3.2 | 8 | 16 | O |
| Example 25 | Synthetic Example 5 | 4 | 8 | 18 | O |
| Example 26 | Synthetic Example 6 | 0.8 | 8 | 12 | O |
| Example 27 | Synthetic Example 6 | 1.6 | 8 | 13 | O |
| Example 28 | Synthetic Example 6 | 2.4 | 8 | 14 | O |
| Example 29 | Synthetic Example 6 | 3.2 | 8 | 16 | O |
| Example 30 | Synthetic Example 6 | 4 | 8 | 18 | O |
| Example 31 | Synthetic Example 7 | 0.8 | 8 | 12 | O |
| Example 32 | Synthetic Example 7 | 1.6 | 8 | 13 | O |
| Example 33 | Synthetic Example 7 | 2.4 | 8 | 14 | O |
| Example 34 | Synthetic Example 7 | 3.2 | 8 | 16 | O |
| Example 35 | Synthetic Example 7 | 4 | 8 | 18 | O |
| Example 36 | Synthetic Example 8 | 0.8 | 8 | 12 | O |
| Example 37 | Synthetic Example 8 | 1.6 | 8 | 13 | O |
| Example 38 | Synthetic Example 8 | 2.4 | 8 | 14 | O |
| Example 39 | Synthetic Example 8 | 3.2 | 8 | 16 | O |
| Example 40 | Synthetic Example 8 | 4 | 8 | 18 | O |
| Example 41 | Synthetic Example 1 | 0.5 | 8 | 11 | O |
| Example 42 | Synthetic Example 1 | 5 | 8 | 18 | O |
| Example 43 | Synthetic Example 2 | 0.5 | 8 | 11 | O |
| Example 44 | Synthetic Example 2 | 5 | 8 | 19 | O |
| Example 45 | Synthetic Example 3 | 0.5 | 8 | 11 | O |
| Example 46 | Synthetic Example 3 | 5 | 8 | 19 | O |
| Example 47 | Synthetic Example 4 | 0.5 | 8 | 11 | O |
| Example 48 | Synthetic Example 4 | 5 | 8 | 19 | O |
| Example 49 | Synthetic Example 5 | 0.5 | 8 | 11 | O |
| Example 50 | Synthetic Example 5 | 5 | 8 | 19 | O |
| Example 51 | Synthetic Example 6 | 0.5 | 8 | 11 | O |
| Example 52 | Synthetic Example 6 | 5 | 8 | 18 | O |
| Example 53 | Synthetic Example 6 | 0.5 | 8 | 11 | O |
| Example 54 | Synthetic Example 7 | 5 | 8 | 19 | O |
| Example 55 | Synthetic Example 7 | 0.5 | 8 | 11 | O |
| Example 56 | Synthetic Example 8 | 5 | 8 | 19 | O |
| Comparative Example 1 | Formula 14 | 0.8 | 8 | 12 | O |
| Comparative Example 2 | Formula 14 | 1.6 | 0 | 13 | O |
| Comparative Example 3 | Formula 14 | 2.4 | 0 | 14 | O |
| Comparative Example 4 | Formula 14 | 3.2 | 0 | 16 | O |
| Comparative | Formula | 4 | 0 | 18 | O |

| Classification | Acrylate-based compound | Content of the acrylate-based compound (weight ratio) | Use content of the binder (weight ratio) | Viscosity (cSt) | Patterning experiment |
|---|---|---|---|---|---|
| Example 5 | 14 | | | | |
| Comparative Example 6 | — | 0 | 0 | 11 | ○ |
| Comparative Example 7 | Synthetic Example 1 | 0.8 | 0 | 2.5 | X |
| Comparative Example 8 | Synthetic Example 2 | 0.8 | 0 | 2.5 | X |
| Comparative Example 9 | Synthetic Example 3 | 0.8 | 0 | 2.5 | X |
| Comparative Example 10 | Synthetic Example 4 | 0.8 | 0 | 2.5 | X |
| Comparative Example 11 | Synthetic Example 5 | 0.8 | 0 | 2.5 | X |
| Comparative Example 12 | Synthetic Example 6 | 0.8 | 0 | 2.5 | X |
| Comparative Example 13 | Synthetic Example 7 | 0.8 | 0 | 2.5 | X |
| Comparative Example 14 | Synthetic Example 8 | 0.8 | 0 | 2.5 | X |

As described above, since the acrylate-based compound according to the exemplary embodiment of the present invention includes at least one organic acid group and at least two acrylate groups simultaneously with the benzene or anthracene structure as the center, the compound may be more usefully applied to the photosensitive composition. The photosensitive composition according to the exemplary embodiment of the present invention may shorten the developing time in a photolithography process without damaging photosensitivity.

What is claimed is:

1. An acrylate-based compound represented by the following Formula 1:

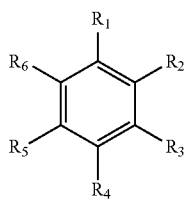

[Formula 1]

wherein
at least one of $R_1$ to $R_6$ is —OH,
at least three of $R_1$ to $R_6$ are each independently represented by the following Formula 2 or Formula 3, and
the rest are selected from the group consisting of hydrogen, a halogen group, an alkyl group having 1 to 5 carbon atoms, an alkoxy group having 1 to 5 carbon atoms, and a haloalkyl group having 1 to 5 carbon atoms,

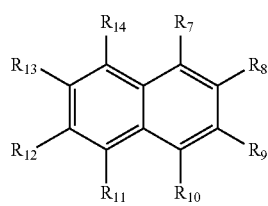

[Formula 2]

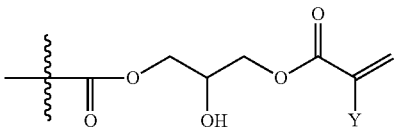

[Formula 3]

wherein
X and Y are each independently selected from the group consisting of hydrogen, a halogen group, an alkyl group having 1 to 5 carbon atoms, an alkoxy group having 1 to 5 carbon atoms, and a haloalkyl group having 1 to 5 carbon atoms.

2. The acrylate-based compound according to claim 1, wherein the Formula 2 is Formula 6 or Formula 7, and the Formula 3 is Formula 8 or Formula 9:

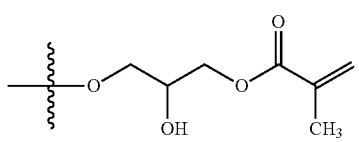

[Formula 6]

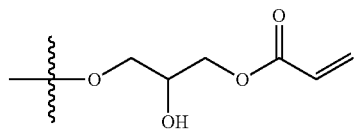

[Formula 7]

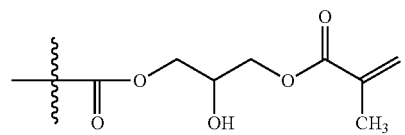

[Formula 8]

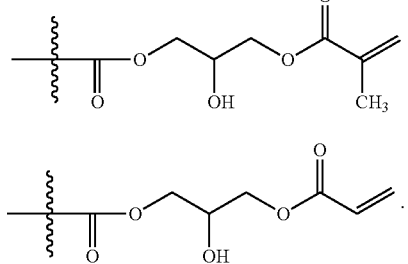

[Formula 9]

3. An acrylate-based compound represented by the following Formula 4:

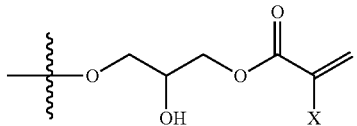

[Formula 4]

wherein
at least one of $R_7$ to $R_{14}$ is —OH,
at least one of $R_7$ to $R_{14}$ is represented by the following Formula 2 and at least one of $R_7$ to $R_{14}$ is represented by the following Formula 3, and
the rest are selected from the group consisting of hydrogen, a halogen group, an alkyl group having 1 to 5 carbon atoms, an alkoxy group having 1 to 5 carbon atoms, and a haloalkyl group having 1 to 5 carbon atoms,

[Formula 2]

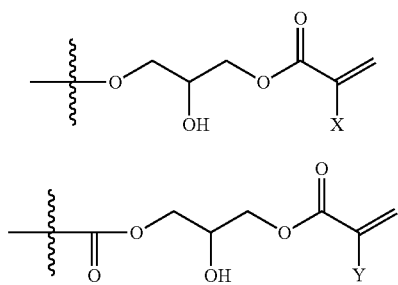

[Formula 3]

wherein

X and Y are each independently selected from the group consisting of hydrogen, a halogen group, an alkyl group having 1 to 5 carbon atoms, an alkoxy group having 1 to 5 carbon atoms, and a haloalkyl group having 1 to 5 carbon atoms.

4. The acrylate-based compound according to claim 3, wherein the Formula 2 is Formula 6 or Formula 7, and the Formula 3 is Formula 8 or Formula 9:

[Formula 6]

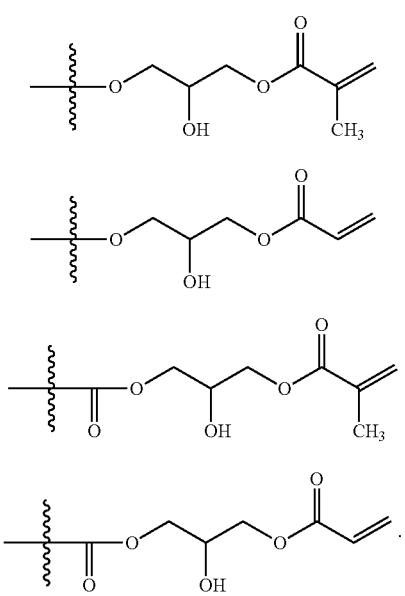

[Formula 7]

[Formula 8]

[Formula 9]

5. An acrylate-based compound represented by the following Formula 5:

[Formula 5]

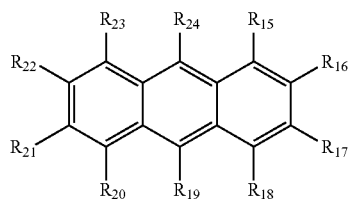

wherein at least one of $R_{15}$ to $R_{24}$ is —OH, at least two of $R_{15}$ to $R_{24}$ are each independently represented by the following Formula 2 or Formula 3, and the rest are selected from the group consisting of hydrogen, a halogen group, an alkyl group having 1 to 5 carbon atoms, an alkoxy group having 1 to 5 carbon atoms, and a haloalkyl group having 1 to 5 carbon atoms,

[Formula 2]

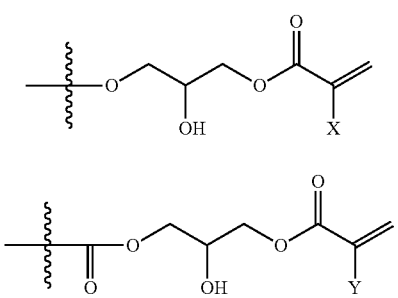

[Formula 3]

wherein

X and Y are each independently selected from the group consisting of hydrogen, a halogen group, an alkyl group having 1 to 5 carbon atoms, an alkoxy group having 1 to 5 carbon atoms, and a haloalkyl group having 1 to 5 carbon atoms.

6. The acrylate-based compound according to claim 5, wherein the Formula 2 is Formula 6 or Formula 7, and the Formula 3 is Formula 8 or Formula 9:

[Formula 6]

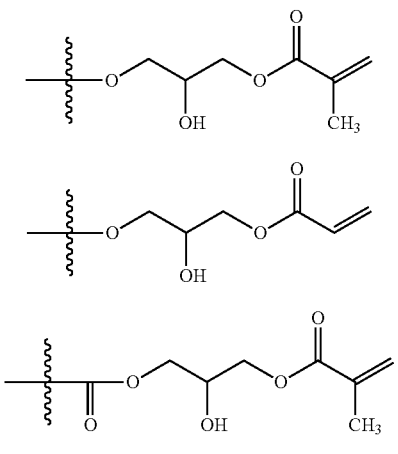

[Formula 7]

[Formula 8]

[Formula 9]

7. A composition for improving a developing property, comprising:

one or more compounds of acrylate-based compounds represented by the following Formula 1, Formula 4, and Formula 5:

[Formula 1]

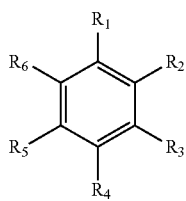

wherein at least one of $R_1$ to $R_6$ is —OH, at least three of $R_1$ to $R_6$ are each independently represented by the following Formula 2 or Formula 3, and the rest are selected from the group consisting of hydrogen, a halogen group, an alkyl group having 1 to 5 carbon atoms, an alkoxy group having 1 to 5 carbon atoms, and a haloalkyl group having 1 to 5 carbon atoms,

[Formula 2]

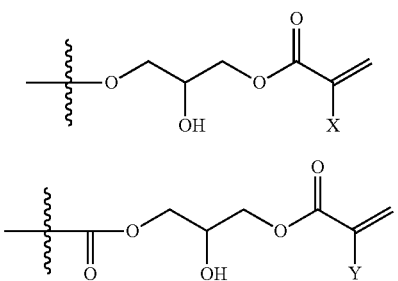

[Formula 3]

wherein

X and Y are each independently selected from the group consisting of hydrogen, a halogen group, an alkyl group having 1 to 5 carbon atoms, an alkoxy group having 1 to 5 carbon atoms, and a haloalkyl group having 1 to 5 carbon atoms,

[Formula 4]

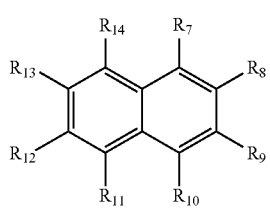

wherein at least one of $R_7$ to $R_{14}$ is —OH, at least one of $R_7$ to $R_{14}$ is represented by the following Formula 2 and at least one of $R_7$ to $R_{14}$ is represented by the following Formula 3, and the rest are selected from the group consisting of hydrogen, a halogen group, an alkyl group having 1 to 5 carbon atoms, an alkoxy group having 1 to 5 carbon atoms, and a haloalkyl group having 1 to 5 carbon atoms,

[Formula 5]

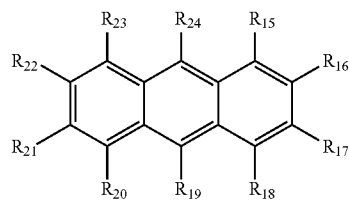

wherein at least one of $R_{15}$ to $R_{24}$ is —OH, at least two of $R_{15}$ to $R_{24}$ are each independently represented by Formula 2 or Formula 3, and the rest are selected from the group consisting of hydrogen, a halogen group, an alkyl group having 1 to 5 carbon atoms, an alkoxy group having 1 to 5 carbon atoms, and a haloalkyl group having 1 to 5 carbon atoms.

8. A photosensitive composition comprising:
a binder resin including an alkali soluble polymer resin;
a crosslinking compound including two or more unsaturated acryl groups;
a photopolymerization initiator;
one or more compounds of acrylate-based compounds represented by the following Formula 1, Formula 4, and Formula 5; and
a solvent:

[Formula 1]

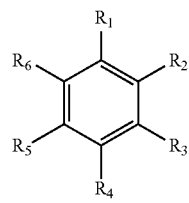

wherein at least one of $R_1$ to $R_6$ is —OH, at least three of $R_1$ to $R_6$ are each independently represented by the following Formula 2 or Formula 3, and the rest are selected from the group consisting of hydrogen, a halogen group, an alkyl group having 1 to 5 carbon atoms, an alkoxy group having 1 to 5 carbon atoms, and a haloalkyl group having 1 to 5 carbon atoms,

[Formula 2]

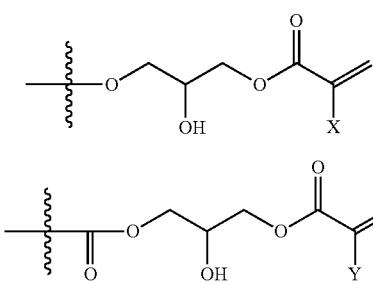

[Formula 3]

wherein

X and Y are each independently selected from the group consisting of hydrogen, a halogen group, an alkyl group having 1 to 5 carbon atoms, an alkoxy group having 1 to 5 carbon atoms, and a haloalkyl group having 1 to 5 carbon atoms,

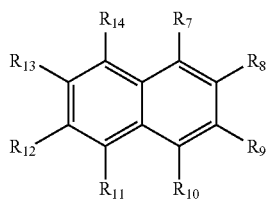

[Formula 4]

wherein at least one of $R_7$ to $R_{14}$ is —OH, at least one of $R_7$ to $R_{14}$ is represented by the following Formula 2 and at least one of $R_7$ to $R_{14}$ is represented by the following Formula 3, and the rest are selected from the group consisting of hydrogen, a halogen group, an alkyl group having 1 to 5 carbon atoms, an alkoxy group having 1 to 5 carbon atoms, and a haloalkyl group having 1 to 5 carbon atoms,

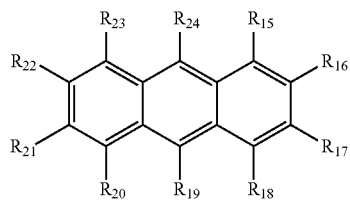

[Formula 5]

wherein at least one of $R_{15}$ to $R_{24}$ is —OH, at least two of $R_{15}$ to $R_{24}$ are each independently represented by Formula 2 or Formula 3, and the rest are selected from the group consisting of hydrogen, a halogen group, an alkyl group having 1 to 5 carbon atoms, an alkoxy group having 1 to 5 carbon atoms, and a haloalkyl group having 1 to 5 carbon atoms.

9. The photosensitive composition according to claim 8, wherein a total content of the acrylate-based compound is 0.8 to 4 wt % on the basis of a total weight of the photosensitive composition.

10. The photosensitive composition according to claim 8, wherein the total content of the acrylate-based compound is 5 to 25 wt % on the basis of a weight of the crosslinking compound.

11. The photosensitive composition according to claim 8, wherein the binder resin is an acryl-based binder resin including a carboxyl group.

12. The photosensitive composition according to claim 8, wherein a content of the binder resin is 1 to 20 wt % on the basis of the total weight of the photosensitive composition.

13. The photosensitive composition according to claim 8, wherein a content of the crosslinking compound is 1 to 30 wt % on the basis of the total weight of the photosensitive composition.

14. The photosensitive composition according to claim 8, wherein a content of the photopolymerization initiator is 0.1 to 5 wt % on the basis of the total weight of the photosensitive composition.

15. The photosensitive composition according to claim 8, wherein a content of the solvent is 45 to 95 wt % on the basis of the total weight of the photosensitive composition.

16. The photosensitive composition according to claim 8, further comprising:
    one or more selected from the group consisting of a colorant, a curing accelerator, a thermal polymerization inhibitor, a surfactant, a photosensitizer, a plasticizer, an adhesion promoter, a filler, and an adhesive preparation.

17. A sensitive material, comprising:
    the photosensitive composition according to claim 8.

18. The sensitive material according to claim 17, wherein the sensitive material is selected from the group consisting of a sensitive material for photoacryl, a sensitive material for a touch panel protection material, a pigment dispersion type sensitive material for manufacturing a color filter, a sensitive material for forming a black matrix, a sensitive material for forming an overcoat layer, a column spacer sensitive material, and a sensitive material for a printed circuit board.

* * * * *